United States Patent [19]
Fujita et al.

[11] Patent Number: 5,413,106
[45] Date of Patent: May 9, 1995

[54] MULTI-DIMENSIONAL VISUALIZATION APPARATUS FOR OBSERVING TISSUE

[75] Inventors: Tatsumori Fujita; Seiji Kondo, both of Tokyo, Japan

[73] Assignee: S.S.B. Co., Ltd., Tsukuba, Japan

[21] Appl. No.: 200,444

[22] Filed: Feb. 23, 1994

[30] Foreign Application Priority Data

Feb. 25, 1993 [JP] Japan ................. 5-059391

[51] Int. Cl.$^6$ ............................................. A61B 8/00
[52] U.S. Cl. ............................ 128/660.07; 128/916
[58] Field of Search ............ 128/660.01, 660.02, 128/660.05, 660.06, 660.07, 660.09, 660.10, 916

[56] References Cited

U.S. PATENT DOCUMENTS

| | | | |
|---|---|---|---|
| 4,567,897 | 2/1986 | Endo et al. | 128/660.07 |
| 4,747,411 | 5/1988 | Ledley | 128/916 |
| 4,787,393 | 11/1988 | Fukukita et al. | 128/660.04 |
| 4,932,414 | 6/1990 | Coleman et al. | 128/916 |
| 5,224,481 | 7/1993 | Ishihara et al. | 128/660.07 |
| 5,282,471 | 2/1994 | Sato | 128/916 |

FOREIGN PATENT DOCUMENTS

| | | |
|---|---|---|
| 0452532A1 | 10/1991 | European Pat. Off. |
| 0487339A1 | 5/1992 | European Pat. Off. |
| 2074733A | 11/1981 | United Kingdom. |
| 91/03792 | 3/1991 | WIPO. |

*Primary Examiner*—George Manuel
*Attorney, Agent, or Firm*—Armstrong, Westerman, Hattori, McLeland & Naughton

[57] ABSTRACT

A multi-dimensional visualization apparatus for observing tissue has a diagnostic apparatus (10) for producing ultrasonic tomographic image data with respect to respective parallel cross sections of tissue to be observed, an image memory (13a) for temporally storing the tomographic image data in the respective cross sections, fed from the diagnostic apparatus, and a computer (14). The computer has a detection function (S13, S14) for detecting layer surface positions in the respective cross sections of the tissue based upon the tomographic image data stored in the memory, to produce layer surface coordinate data indicative of the detected layer surface positions, a coordinate transformation function (S16) for converting the layer surface coordinate data of the respective cross sections into three-dimensional coordinate data, and a display function (S17, S18) for displaying both a three-dimensional image of the layer surface positions in the respective cross sections of the tissue based upon the converted three-dimensional coordinate data and the tomographic image of a desired cross section based upon the tomographic image data stored in the memory, on the same screen.

26 Claims, 15 Drawing Sheets

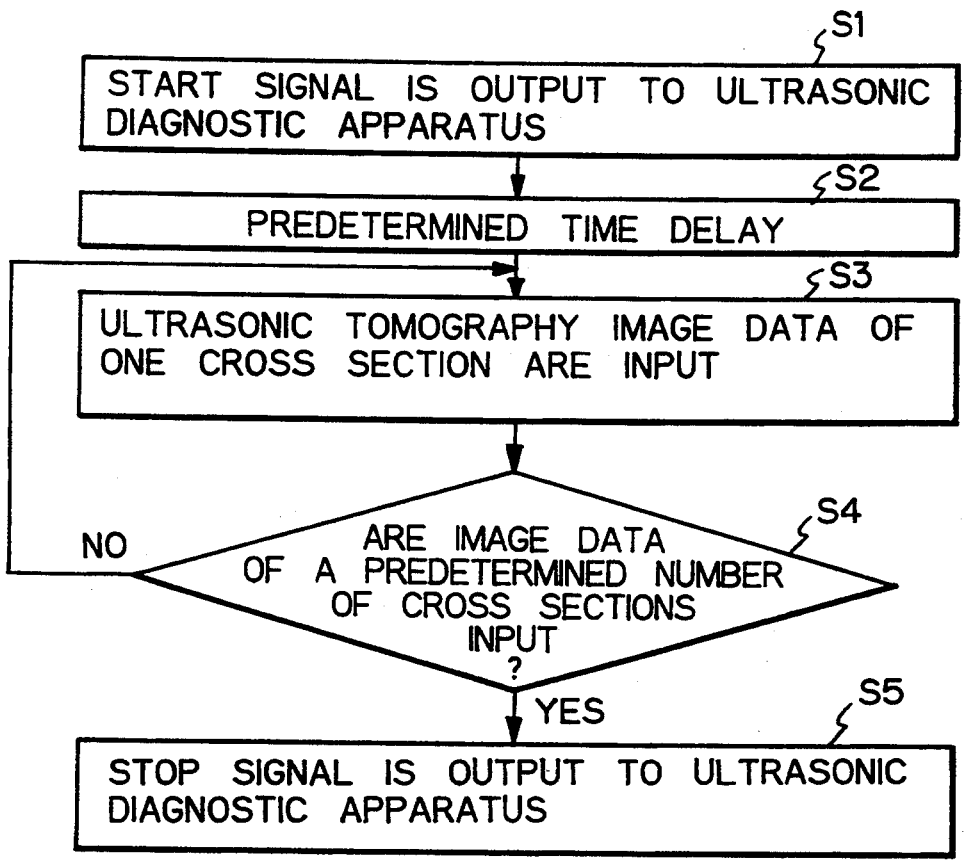
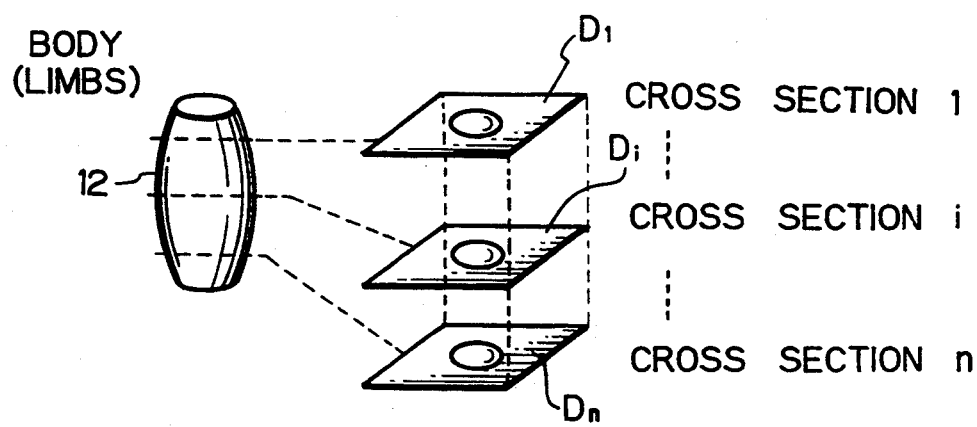

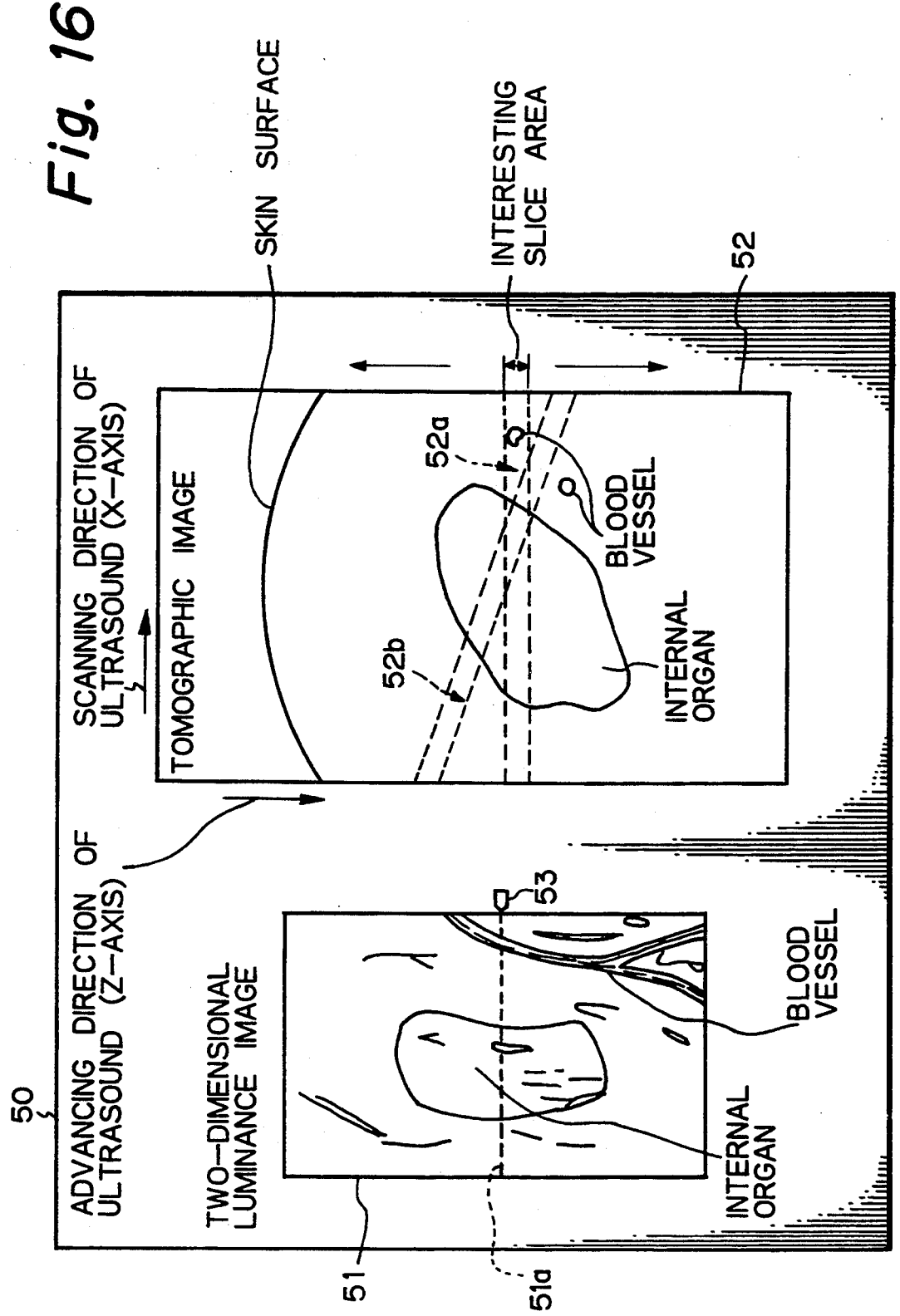

MULTI-DIMENSIONAL VISUALIZATION APPARATUS FOR OBSERVING TISSUE

BACKGROUND OF THE INVENTION

1. Field of the Invention

The present invention relates to a multi-dimensional visualization apparatus for observing tissue within a body by using a function of producing ultrasonic tomographic images provided for example in an ultrasonic diagnostic apparatus.

2. Description of the Related Art

The ultrasonic diagnostic apparatus can produce a tomographic image of tissue in a cross section of a body, scanned by its ultrasound probe in contact with the body surface. In order to produce tile ultrasonic tomographic image of, for example, a certain tissue at a particular depth within the body, following operations will be executed. First, the linear-scanning type probe of tile ultrasonic diagnostic apparatus is contacted with the body surface near the tissue. Then, a pulsated ultrasound beam is directed into the body from the probe and the reflected echo is received by the probe. The intensity of this received echo is then displayed along a time axis. By linearly scanning the above-mentioned ultrasound beam from the probe, a single tomographic image can be displayed. For diagnosis of the tissue, it is necessary to observe a plurality of the tomographic images which are produced by displacing the probe perpendicularly to its linear-scanning direction.

According to the conventional ultrasonic diagnosis, a medical doctor is used to find abnormal portions within the body and examines pathologic changes by observing a large number of tomographic images. Therefore, it is necessary for such the diagnosis to have special and high-degree experience and also special skill. In other words, only a medical doctor specially trained can examine the tomographic images.

Furthermore, the conventional ultrasonic diagnostic apparatus is a one utilized mainly for observing viscera, not for observing bone, tendon or muscle tissues of the body. No apparatus can easily observe bone, tendon or muscle tissues without the assistance of expert image-examination technique. Although bone structure of the limbs can be observed by means of radiography, a special qualification will be necessary for treating X-ray and also there may be harmful of X-ray radiation.

SUMMARY OF THE INVENTION

It is therefore an object of the present invention to provide a multi-dimensional visualization apparatus for observing tissue which makes it possible to easily observe tissue without the assistance of expert image-examination technique.

According to the present invention, a multi-dimensional visualization apparatus for observing tissue is provided with a diagnostic apparatus for producing ultrasonic tomographic image data with respect to respective parallel cross sections of tissue to be observed, and an image memory for temporally storing the tomographic image data in the respective cross sections, fed from the diagnostic apparatus. The multi-dimensional visualization apparatus is further provided with a digital computer having a function for detecting layer surface positions in the respective cross sections of the tissue based upon the tomographic image data stored in the memory, to produce layer surface coordinate data indicative of the detected layer surface positions, a coordinate transformation function for converting the layer surface coordinate data of the respective cross sections into three-dimensional coordinate data, and a function for displaying both a three-dimensional image of the layer surface positions in the respective cross sections of the tissue based upon the converted three-dimensional coordinate data and the tomographic image of a desired cross section based upon the tomographic image data stored in the memory, on the same screen.

Since a three-dimensional layer surface image is displayed next to the tomographic image of the desired cross section on the same screen, relationship between the tomographic image and the three-dimensional layer surface image can be directly and concretely recognized so that analysis of injury changes of tissues such as tendon of soft tissue or muscle connective tissue can be easily executed without the assistance of expert image-examination technique.

It is preferred that the coordinate transformation function converts the layer surface coordinate data of the respective cross sections into three-dimensional coordinate data of lines for the respective cross sections, and the displaying function displays both a three-dimensional image of the layer surface positions In the respective cross sections by the respective lines and the tomographic image of the desired cross section, on the same screen.

Preferably, the displaying function indicates a particular line of the desired cross section so that this line can be identified from the remaining displayed lines.

The above-indication of the line may be indication of a line with a different color from that of the remaining displayed lines, of a blinking line, of a line with a different width from that of the remaining displayed lines, or of a line with a different style from that of the remaining displayed lines.

According to the present invention, furthermore, a multi-dimensional visualization apparatus for observing tissue has a diagnostic apparatus for producing ultrasonic tomographic image data with respect to respective parallel cross sections of tissue to be observed, which ultrasonic tomographic image data the each cross section are constituted by a plurality of pixel data to be arranged in an ultrasound advancing direction and an ultrasound scanning direction, and an image memory for temporally storing the tomographic image pixel data in the respective cross sections, fed from the diagnostic apparatus. The multi-dimensional visualization apparatus also has a digital computer provided with a function for calculating average values of the stored tomographic image pixel data along the ultrasound advancing direction within a designated interesting area. This calculation of the average values is executed in the every cross sections of the tissue to produce two-dimensional image data. The computer further has a function for displaying both a two-dimensional image of the tissue based upon the produced two-dimensional image data and the tomographic image of a desired cross section based upon the tomographic image data stored in the image memory, on the same screen.

It is preferred that displaying function displays the tomographic image of the desired cross section and the two-dimensional image with a mark for indicating a position of the displayed cross section, on the same screen.

Preferably, the displaying function displays the two-dimensional image in various luminance intensities or different colors depending upon the produced two-dimensional image data.

It is preferred that the computer further has a function for detecting layer surface positions in the respective cross sections of the tissue based upon the tomographic image pixel data stored in the image memory, to produce layer surface coordinate data indicative of the detected layer surface positions, and a function for deleting the tomographic image pixel data stored in the image memory, in the respective cross sections of the tissue based upon the layer surface coordinate data and a designated surface compensation value.

The designated interesting area may be specified by at least the layer surface coordinate data and a desired variable depth, or may be a designated interesting slice area with a strip shape.

Preferably, the computer also has a function for moving the interesting slice area in the ultrasound advancing direction to a next designated area.

The interesting slice area may be extending in parallel with the ultrasound scanning direction, or inclined to the ultrasound scanning direction.

Preferably, the detecting function includes a function for eliminating low leveled echo component from contents of the tomographic image data stored in the memory. This eliminating function may also include a function for forcibly changing contents of pixel data of the tomographic image, having values equal to or less than a predetermined value, to zero.

It is preferred that the detecting function includes a function for comparing values of the neighboring pixel data of the tomographic image data in sequence along an ultrasound advancing direction to detect a position where a difference between the compared values changes to a value larger than zero.

The apparatus may further includes a thermal video observation device for measuring thermal distribution on a body surface, and the computer may have a function for displaying the measured thermal distribution on the same screen as the tomographic image.

The apparatus may further includes a moire pattern observation device for producing a moire pattern on a body surface, and the computer may have a function for simultaneously displaying an image indicating outside changes of the body surface obtained from the moire pattern device and the tomographic image on the same screen.

Further objects and advantages of the present invention will be apparent from the following description of the preferred embodiments of the invention as illustrated in the accompanying drawings.

BRIEF DESCRIPTION OF THE DRAWINGS

FIG. 3 is a flow chart of a control program for controlling an input of ultrasonic tomographic image data;

FIG. 4 illustrates a relationship between a body (limbs) and its tomographic images;

FIG. 16 illustrates an example of an image displayed by the program of FIG. 14.

DESCRIPTION OF THE PREFERRED EMBODIMENTS

Figure 1:
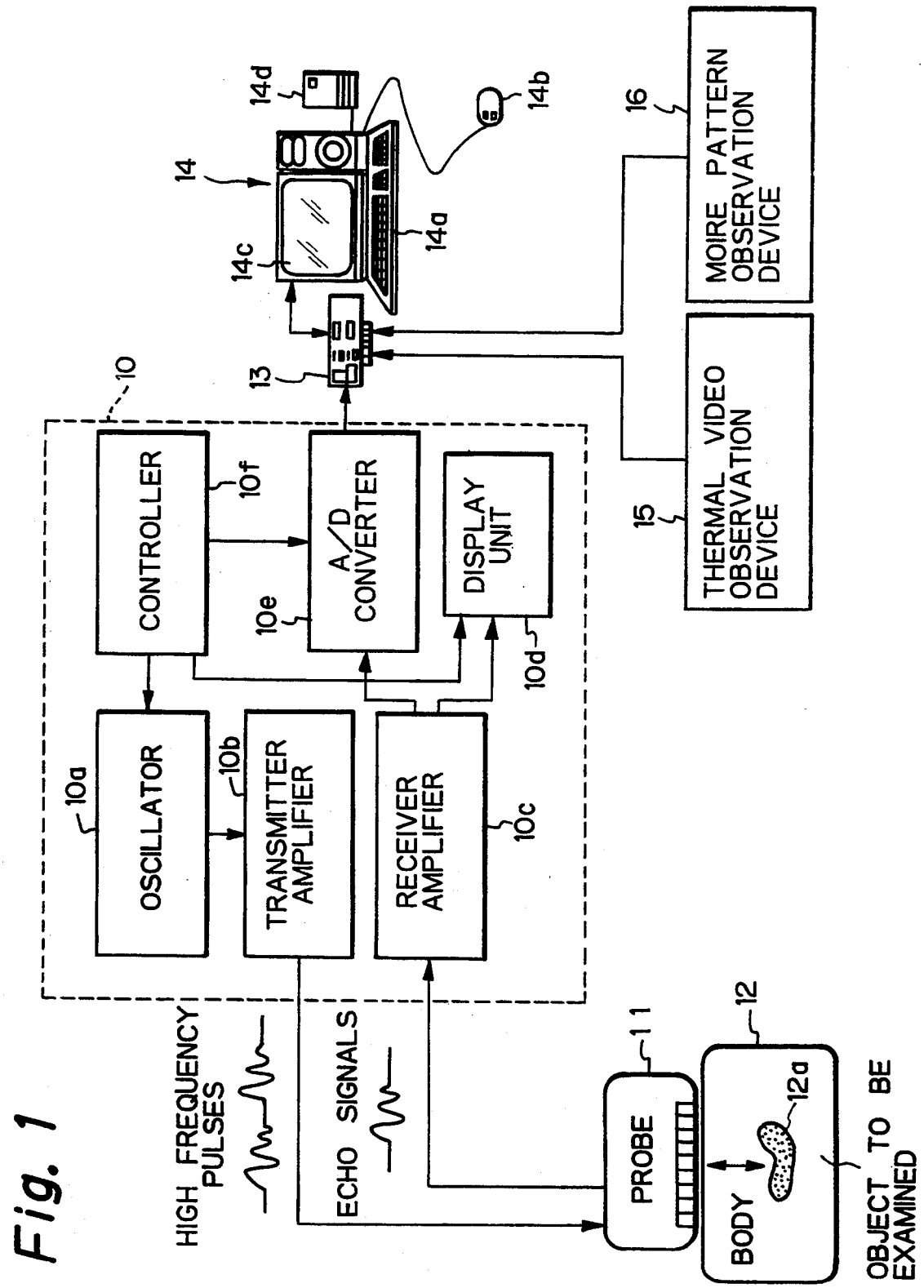
FIG. 1 is a block diagram schematically showing a preferred embodiment of a multi-dimensional visualization apparatus for observing tissue according to the present invention.

FIG. 1 schematically shows a preferred embodiment of a multi-dimensional visualization apparatus for observing tissue according to the present invention.

In the figure, reference numerals 10 denotes an ultrasonic diagnostic apparatus, and 11 denotes a probe of this ultrasonic diagnostic apparatus 10. The diagnostic apparatus 10 has the same constitution as that of a general ultrasonic diagnostic apparatus on the market. Namely, as shown in the figure, it includes an oscillator 10a for generating high frequency pulsated voltage, a transmitter amplifier 10b for amplifying the voltage and outputting high frequency pulses to the probe 11, a receiver amplifier 10c for receiving and amplifying reflected pulses (echo signals) fed from the probe 11, a display unit 10d such as a liquid crystal display device or a CRT for displaying the output from the receiver amplifier 10c, an A/D converter 10e for converting the output from the receiver amplifier 10c into digital data, and a controller 10f for executing another control such as synchronization of the high frequency pulses to be transmitted with the display unit 10d and the A/D converter 10e, and as selection of the oscillation frequency.

The oscillation frequency at the oscillator 10a will be selected depending upon a kind of an object 12a to be examined in a body 12, for example depending upon whether it is bone or muscle. According to this embodiment, the apparatus is constituted as that this frequency can be selected from 3.5 MHz, 5.0 MHz and 7.5 MHz. The probe 11 may be changed to another one for matching with the oscillated frequency.

The probe 11 is a linear-scanning type ultrasound probe having a large number of aligned piezoelectric oscillation elements. During operation, this probe 11 is maintained in contact with the skin surface of the body 12 to be examined through a water balloon (not shown) or jellied oil applied on the body surface (not shown). High frequency pulses fed from the diagnostic apparatus 10 to the probe 11 are selectively applied to each of the aligned piezoelectric elements in sequence. Thus, ultrasound pulses are directed into the body 12 from each of the piezoelectric elements. Ultrasound echo reflected by the object 12a to be examined within the body 12 are received by each of the piezoelectric elements and converted into electric pulses called as echo signals. These echo signals are then fed from the probe 11 to the diagnostic apparatus 10.

An output terminal of the A/D converter 10e in the ultrasonic diagnostic apparatus 10 is coupled to an input interface (not shown) in a digital computer 14 such as a personal computer for example via a control board 13. The computer 14 is provided with a CPU (Central Processing Unit), ROMs (Read Only Memories) for storing various programs described later, RAMs (Random Access Memories), buses for connecting them and another general control circuits, not shown. The computer 14 also has in general, as shown in FIG. 1, an input unit such as a keyboard 14a and a mouse 14b, a CRT 14c and an external memory 14d.

Figure 2:
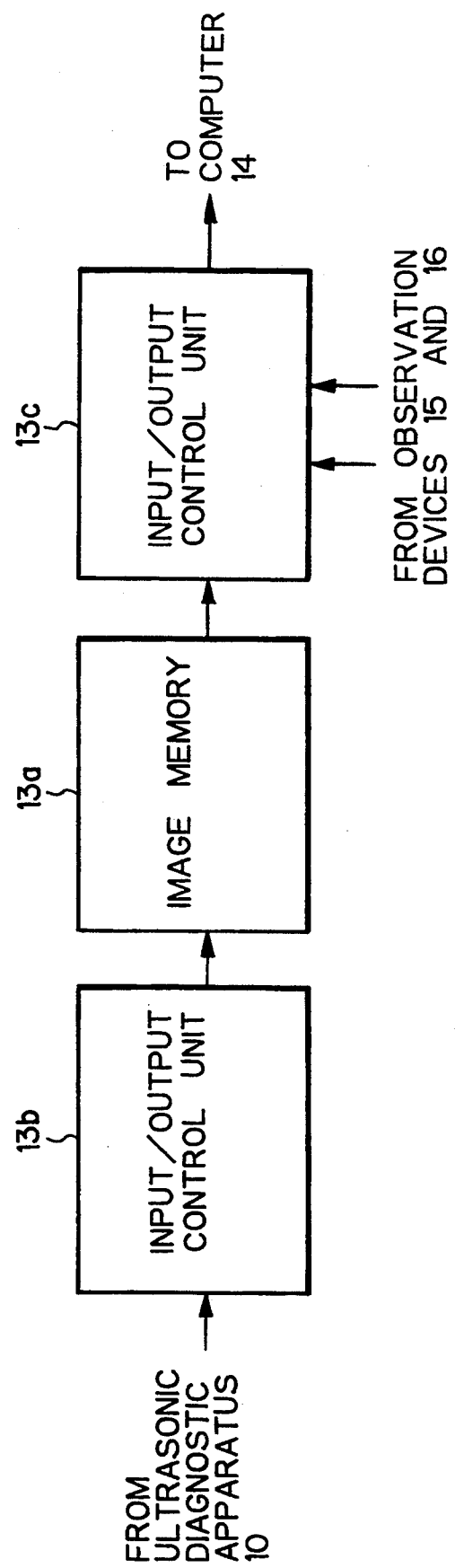
FIG. 2 is a block diagram schematically showing a constitution of a control board shown in FIG. 1.

As shown in FIG. 2, the control board 13 includes an image memory 13a for temporally storing tomographic image data fed from the ultrasonic diagnostic apparatus 10 to operate as a circulating buffer between the diagnostic apparatus 10 and the digital computer 14. This memory 13a can be constructed by general RAM or RAMs. In this embodiment, the memory 13a has a capacity capable of storing one hundred of tomographic images. If image data over this capacity are input into the memory 13a, the data will be overwritten on the memory 13a from the leading address in sequence, so that newest data of one hundred tomographic images will be always stored.

Input/output control units 13b and 13c are connected to in front and rear of the image memory 13a, respectively. To the input/output control unit 13c, a thermal video observation device 15 capable of measuring thermal distribution on the body surface and a moire pattern observation device 16, shown in FIG. 1, are connected so that the computer 14 can introduce necessary data from each of the devices 15 and 16 during certain modes.

Hereinafter, operation of this embodiment will be described based upon flow charts with respect to the digital computer 14.

FIG. 3 is a flow chart of a control program for controlling an input of ultrasonic tomographic image data.

When an operator applies a command for inputting ultrasonic tomographic image data to the computer 14 by means of the keyboard 14a or the mouse 14b, a start signal is output to the ultrasonic diagnostic apparatus 10 at step S1. At the next step S2, the start of inputting the image data will be delayed for a predetermined time so as to make up for the time difference between the command for inputting the data and an actual start of movement of the probe 11.

While the probe 11 is moved, in contact with a layer surface of the body 12, along a certain axis at a constant speed by means of the operator or an automatic feeding mechanism (not shown), processes at steps S3 and S4 are performed. At the step S3, an ultrasonic diagnosis similar to that of the conventional diagnosis is executed and thus ultrasonic tomographic image data for one screen, namely ultrasonic tomographic image data of one cross section, are output from the diagnostic apparatus 10 and input to the control board 13. The input image data are stored in the image memory 13a in the control board 13. At the step S4, it is judged whether the tomographic image data of a predetermined number of cross sections are input and stored in the memory 13a or not. This judgment may be carried out by checking that the amount of the input image data becomes equal to a certain amount, or by checking that a certain time period was elapsed after the start of the diagnosis. The latter may be easy for processing. If the predetermined amount of the image data are not input and stored, the program returns to the step S3. If the image data of the predetermined number of cross sections are input and stored, the program goes to the next step S5.

At the step S5, a stop signal is output to the ultrasonic diagnostic apparatus 10. At this time, ultrasonic tomographic image data of the predetermined number of cross sections have been already stored in the image memory 13a. In other words, as shown in FIG. 4, tomographic image data concerning different cross sections $D_1$ to $D_n$ of the body 12 are being stored in the image memory 13a.

Figure 5:
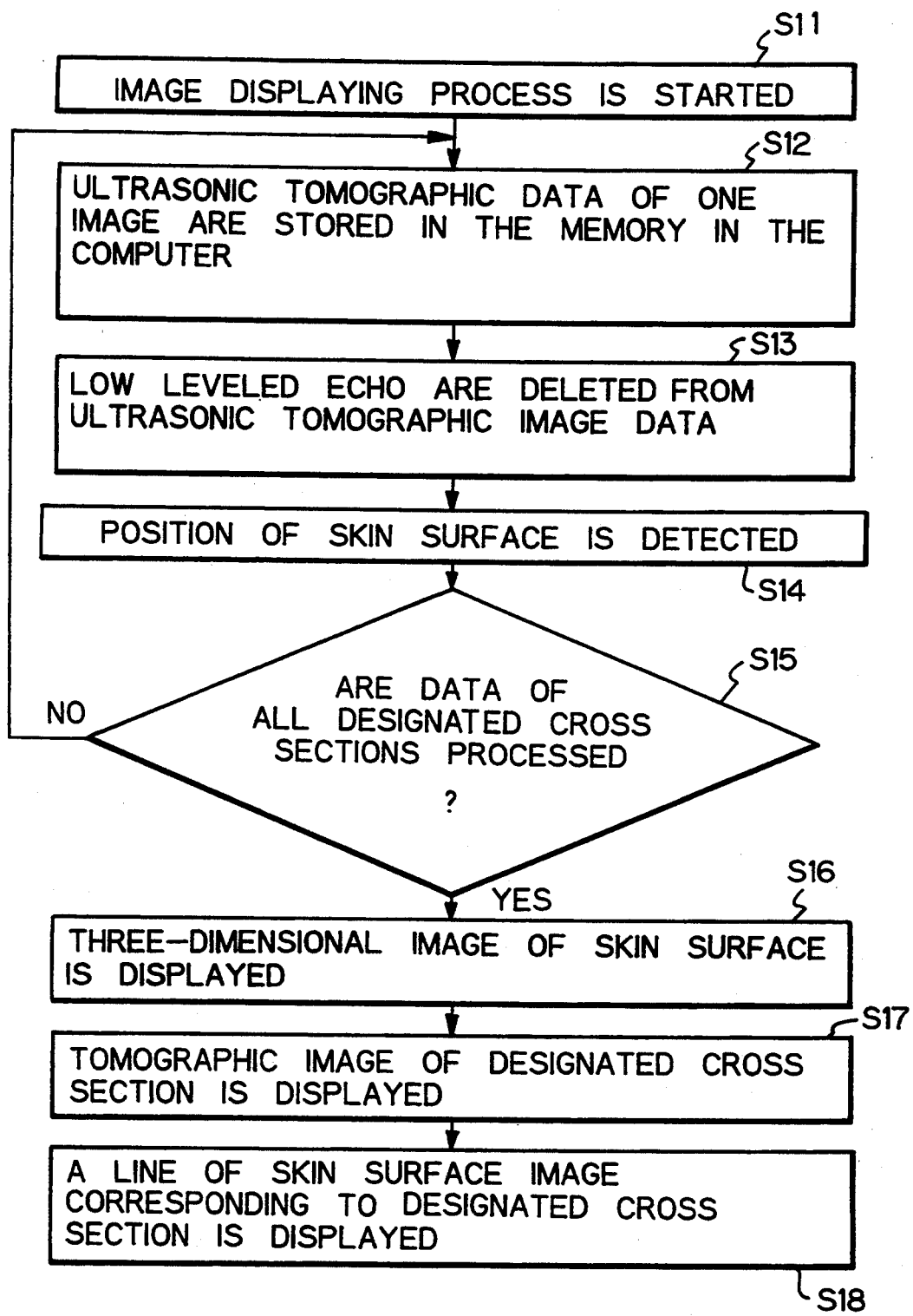
FIG. 5 is a flow chart of a control program for controlling display of images.

FIG. 5 is a flow chart of a control program for controlling a display of images.

When the operator applies a command for displaying tomographic image to the computer 14 by means of the keyboard 14a or the mouse 14b, an image displaying process will be started at step S11. At the next step S12, ultrasonic tomographic image data of one image (of one cross section) are read out from the image memory 13a in the control board 13 and stored in a RAM in the computer 14.

Then, at step S13, low leveled echo portions are deleted from the stored tomographic image data so as to eliminate noise component occurred when the ultrasound passed between the probe 11 and the skin surface. This process at the step S13 will be hereinafter described in detail with reference to FIGS. 6 and 7.

Figure 6:
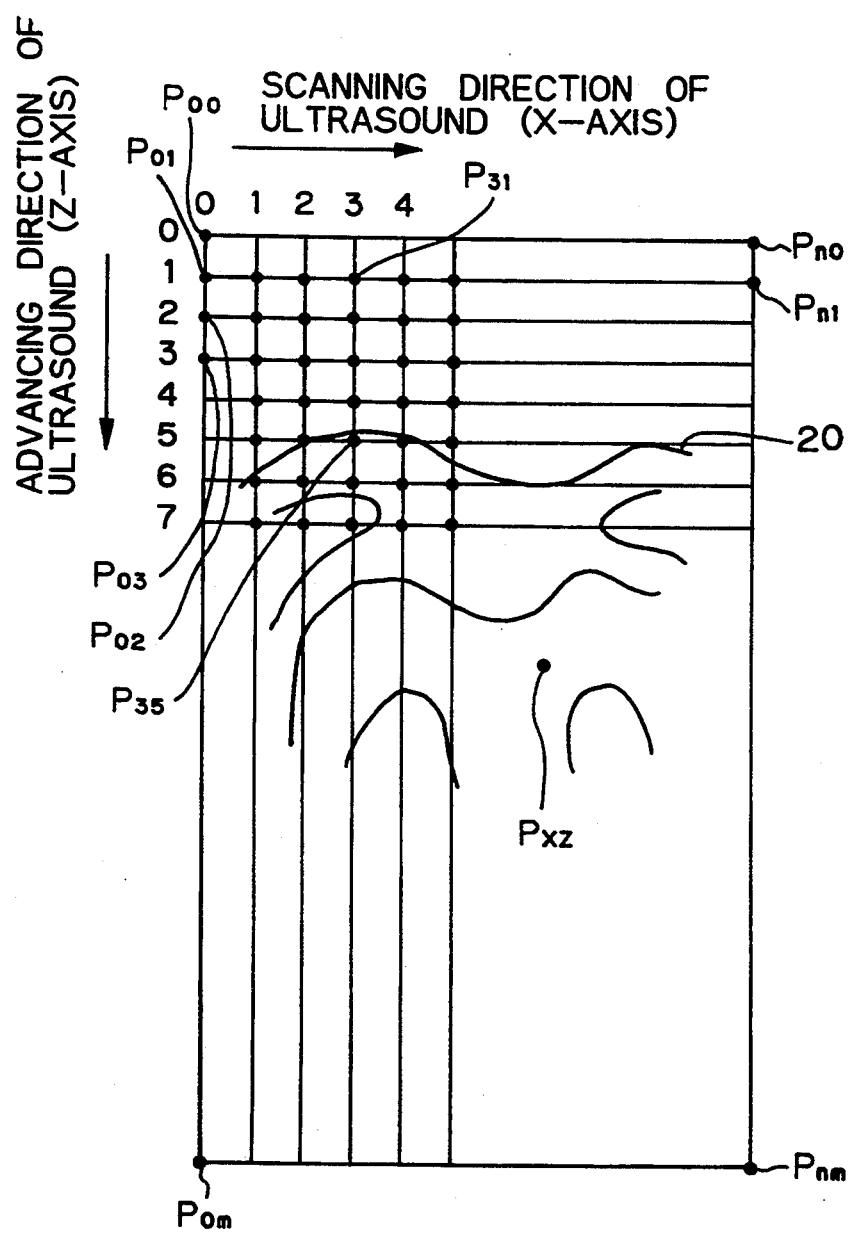
FIG. 6 illustrates a relationship between an image in one cross section and its ultrasonic tomographic image data.
Figure 7:
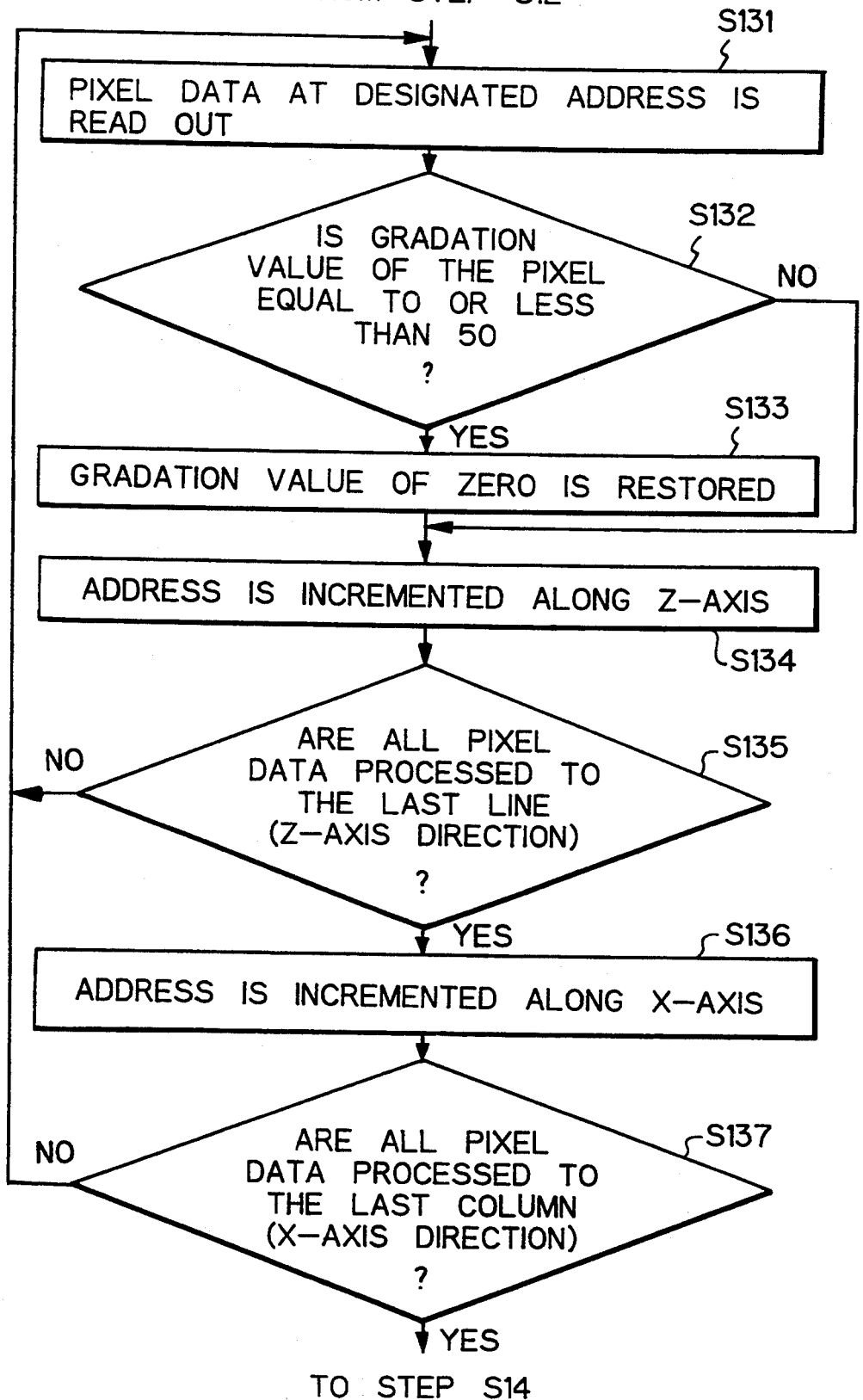
FIG. 7 is a flow chart showing a process of deleting low-leveled echo, in the program shown in FIG. 5.

FIG. 6 illustrates a relationship between an image of one cross section and its ultrasonic tomographic image data for understanding following description and FIG. 7 is a flow chart showing the process at the step S13. It is supposed that, as shown in FIG. 6, ultrasonic tomographic image data of one cross section are constituted by a large number of pixel data $P_{xz}$ arranged in a matrix along a scanning direction of ultrasound (X-axis) and also along an advancing direction of ultrasound (Z-axis).

At step S131 of FIG. 7, an address pointer of the computer 14 designates the leading address of the ultrasonic tomographic image data area in the RAM, and thus a pixel data $P_{00}$ stored in that address is read out. Each of the pixel data $P_{xz}$ has one of gradation values "0" to "255" depending upon its echo level.

At the next step S132, whether the gradation value of the read out pixel data $P_{00}$ is equal to or less than "50" or not is judged. If the gradation value of the pixel data is equal to or less than "50", the program proceeds to step S133. At the step S133, the gradation value of this pixel data is forcibly changed to zero and then this value is restored in the RAM at the same address. At the next step S134, the address is incremented along the Z-axis (advancing direction of ultrasound) to an address corresponding to a location of a pixel data $P_{01}$ on the next line.

At step S135, it is judged whether the above-mentioned processes at the steps S131 to S133 are performed with respect to all the pixel data $P_{01}$, $P_{02}$, $P_{03}$ ..., $P_{0m}$ on the leading column or not. If not, the program returns to the step S131 and the same processes at the steps S131 to S134 are executed against the remaining pixel data on this column. If the processes are completed for all the pixel data $P_{01}$, $P_{02}$, $P_{03}$, ..., $P_{0m}$ on the column, the program will proceed to step S136. At the step S136, the address is incremented along the X-axis (scanning direction of ultrasound) to an address corresponding to a location of a pixel data $P_{10}$ on the leading line of the next column.

At the next step S137, it is judged whether the above-mentioned processes at the steps S131 to S136 are performed to all the pixel data on the last column or not. If not, the program returns to the step S131 and the same processes at the steps S131 to S136 are executed against the remaining pixel data. If the processes are completed for all the pixel data $P_{n0}$, $P_{n1}$, ..., $P_{nm}$ on the last column, the program will proceed to step S14 of the program shown in FIG. 5.

Figure 8:
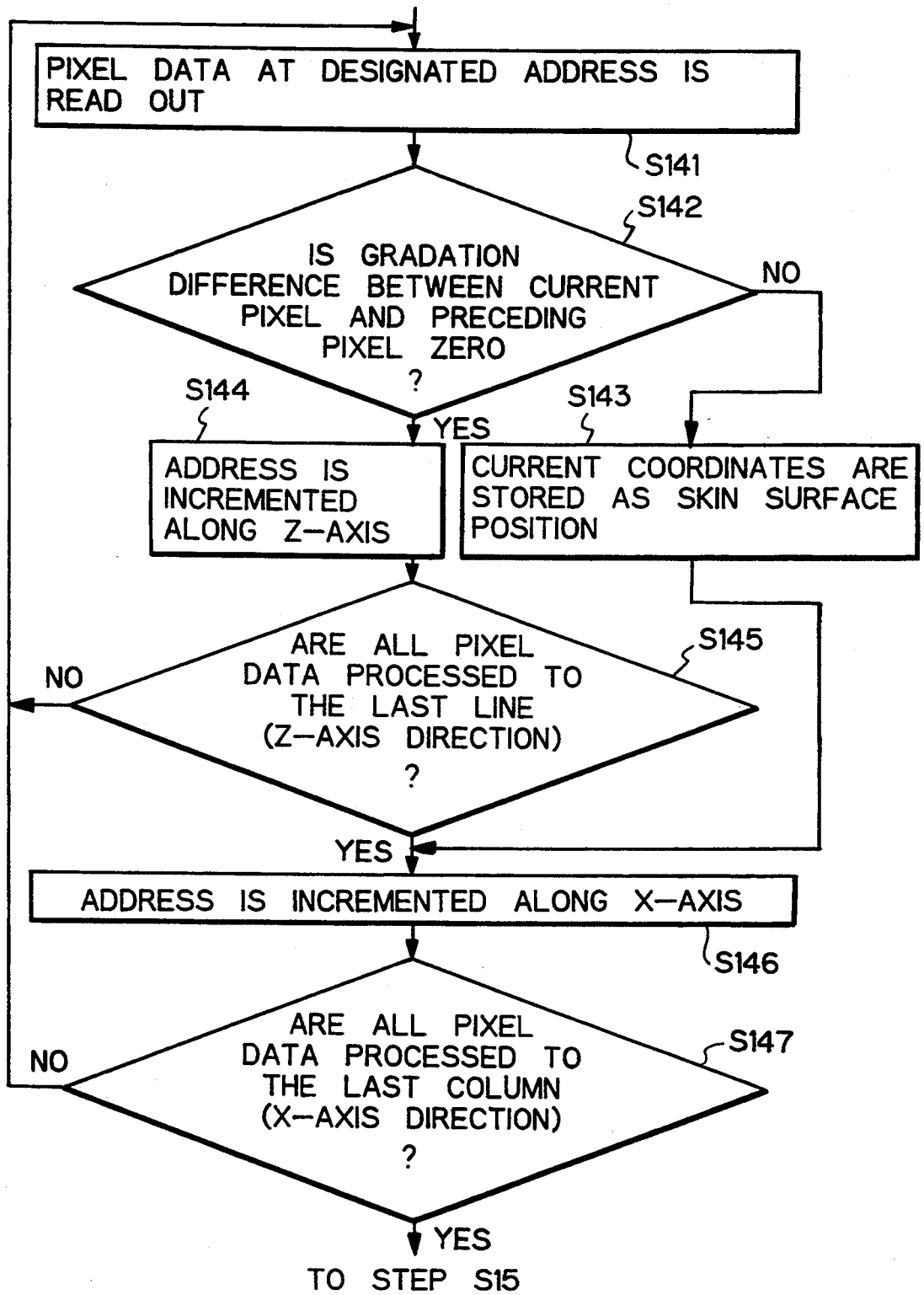
FIG. 8 is a flow chart showing a process of detecting a position of skin surface, in the program shown in FIG. 5.

At step S14, coordinates of the layer surface or the skin surface will be detected. This detection is executed by comparing gradation values of the neighboring pixels of the ultrasonic tomographic image data in sequence along the ultrasound advancing direction to know a position where the difference first becomes a value larger than zero. This position will be recognized as a position on the body surface. FIG. 8 shows this process of detecting the skin surface positions in detail.

At step S141 of FIG. 8, the pointer designates to the leading address of the ultrasonic tomographic image data area in the RAM of the computer 14, and the pixel data $P_{00}$ stored at that leading address is read out. At the next step S142, it is judged whether the difference between the gradation values of the current pixel and the preceding pixel is zero or not. Only when the gradation difference is a value larger than zero, it is recognized that this position corresponds to the skin surface and the coordinates of the current pixel is stored in the RAM at step S143. If the gradation difference is zero, the program proceeds to step S144 wherein the address is incremented along the Z-axis (advancing direction of ultrasound) to an address corresponding to a location of the pixel data $P_{01}$ on the next line. At the next S145, it is judged whether the above-mentioned processes at the steps S141 and S142 are performed with respect to all the pixel data $P_{01}$, $P_{02}$, $P_{03}$, ..., $P_{0m}$ on the leading column or not. If not, the program returns to the step S141 and the same processes at the steps S141 and S142 are executed against the remaining pixel data on this column. If the processes are completed for all the pixel data $P_{01}$, $P_{02}$, $P_{03}$, ..., $P_{0m}$ on the column or if the gradation difference became a value other than zero and thus the process at the step S143 has been completed, the program will proceed to step S146. At the step S146, the address is incremented along the X-axis (scanning direction of ultrasound) to an address corresponding to a location of a pixel data $P_{10}$ on the leading line of the next column.

At the next step S147, it is judged whether the above-mentioned processes at the steps S141 to S146 are performed to all the pixel data on the last column or not. If nor, the program returns to the step S141 and the same processes at the steps S141 to S146 are executed against the remaining pixel data. If the processes are completed for all the pixel data $P_{n0}$, $P_{n1}$, ..., $P_{nm}$ on the last column, the program will proceed to step S15 of the program shown in FIG. 5.

After the above-mentioned processes of the steps S11 to S14 are completed, coordinate data of a line 20 indicating the skin surface (see FIG. 6) derived from the ultrasonic tomographic image data will be stored in the RAM. Why the skin surface position can be detected is as follows. Since, between the probe 11 and the layer surface of the body, there exist only the jellied oil or the water balloon filled with water, ultrasound beam directed from the probe 11 will be first reflected at the skin surface due to the difference of there sound impedances. Therefore, by searching a position where the gradation difference concerning the echo level changes a value other than zero, the skin surface position can be detected.

At step S15 of FIG. 5, the computer 14 judges whether the aforementioned processes at the steps S12 to S14 are completed for the ultrasonic tomographic data of all the designated images (cross sections) or not. If not, the program returns to the step S12 and the same processes are repeatedly executed. If completed for the all images, the program will proceed to step S16.

At the step S16, the coordinate data of the skiff surface line are converted, by a coordinate transformation, into three-dimensional coordinate data of a line for each image or cross section, and then the converted three-dimensional coordinates are displayed on the CRT 14c. Detailed illustration about the operation of this step S16 is shown in FIG. 9.

Figure 9:
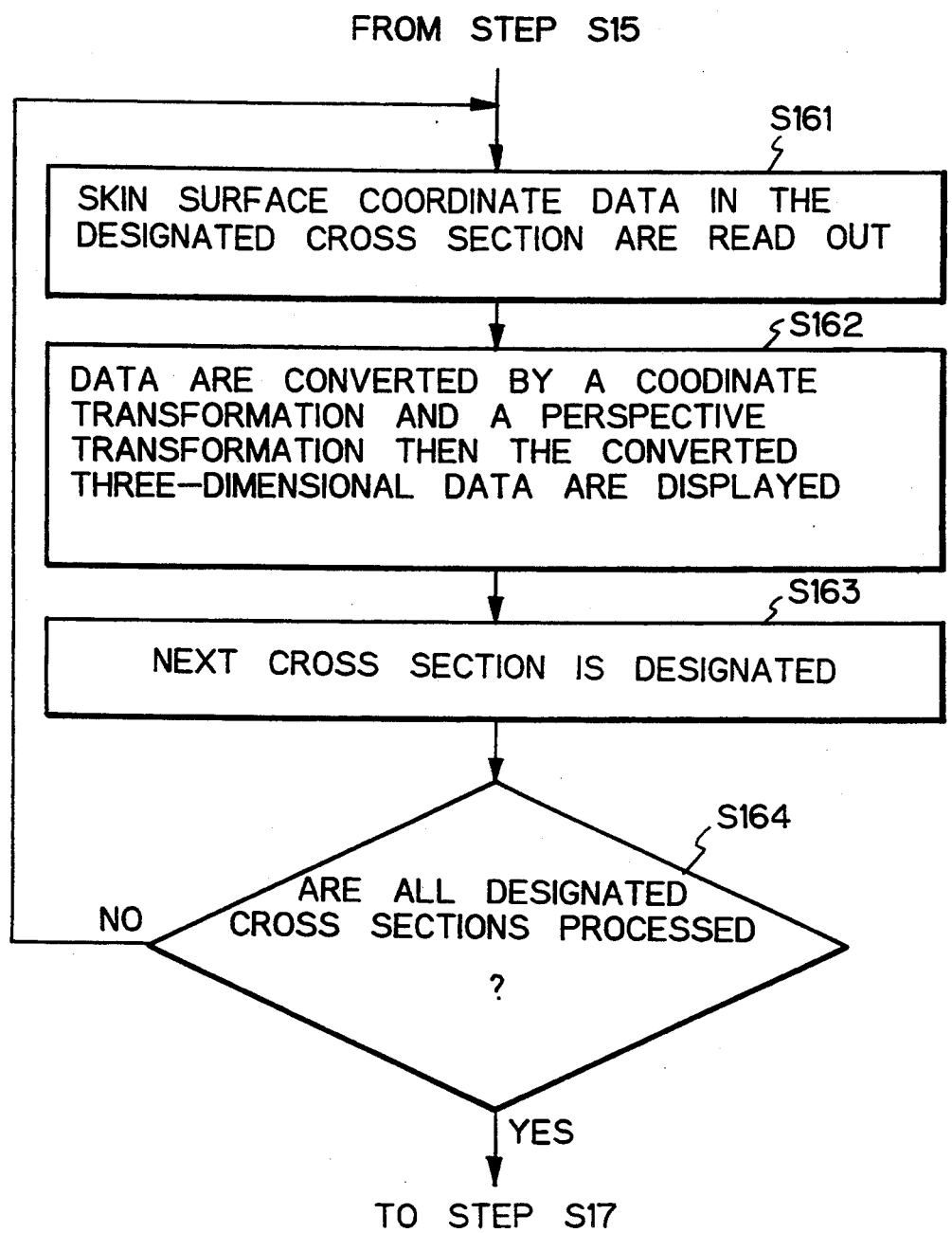
FIG. 9 is a flow chart showing processes of converting coordinate data of the skin surface into three-dimensional coordinate data of each cross section and of displaying a three-dimensional image based upon the converted data, in the program shown in FIG. 5.

At step S161 of FIG. 9, coordinate data of the skin surface (two-dimensional data of one line) in a certain cross section of the body designated by the pointer are read out from the RAM of the computer 14. Then, at step S162, the coordinate data are converted by a coordinate transformation and by a perspective transformation into three-dimensional coordinate data of a single line, and then the converted data are three-dimensionally displayed on the CRT 14c as one line.

At the next step S163, the pointer is incremented so that skin surface data of the next cross section are designated. Thereafter, at step S164, the computer 14 judges whether the aforementioned processes at the steps S161 to S163 are completed for the coordinate data of all the designated cross sections or not. If not, the program returns to the step S161 and the same processes are repeatedly executed. If completed for the all cross sections, the program will proceed to step S17 of FIG. 5.

Figure 10:
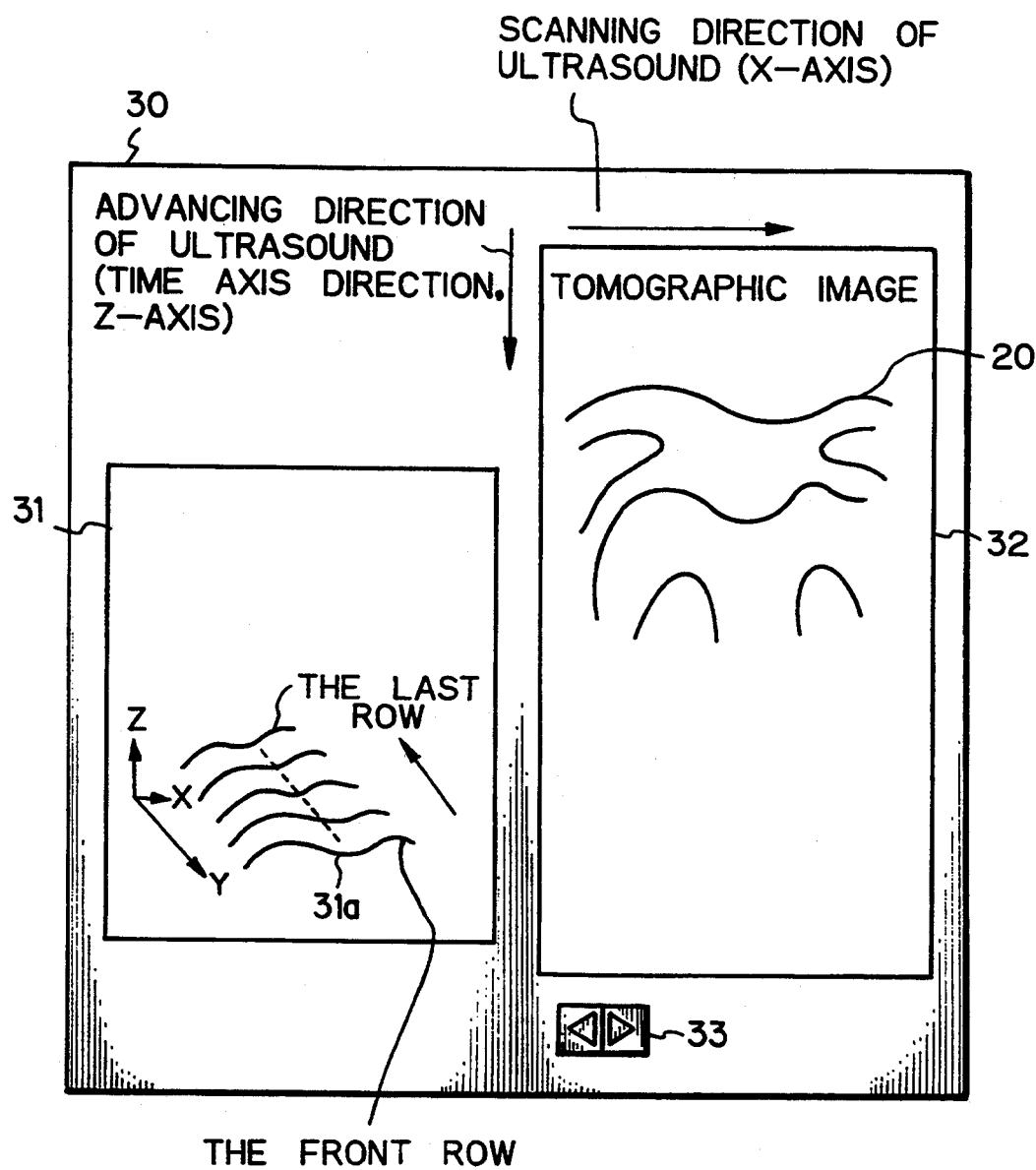
FIG. 10 illustrates an example of an image displayed by the program of FIG. 5.

Thus, as shown in FIG. 10, a three-dimensional image 31 indicating the skin surface is displayed on the CRT 14c of the computer by a plurality of curves which represent the respective cross sections.

At the step S17 of FIG. 5, a tomographic image 32 of the designated cross section, stored in the RAM of the computer 14, is read out and displayed on the same screen 30 as the three-dimensional image 31 of the skin surface, as shown in FIG. 10. According to this embodiment, a tomographic image with respect to a cross section which has been introduced into the ultrasonic diagnostic apparatus 10 at first will be initially displayed. In FIG. 10, this cross section will correspond to the front raw 31a of curved lines in the three-dimensional image 31 of the skin surface. A desired cross section can be designated by accessing an icon 33 on the screen 30 by means of the keyboard 14a or the mouse 14b resulting that a tomographic image corresponding to the designated cross section is displayed on the screen 30.

At the next step S18, a curved line with respect to the designated cross section, of the three-dimensional image 31 of the skin surface is particularly indicated so that this curve can be identified from the remaining displayed curves. As a result, the relationship between the three-dimensional image of the skin surface and the ultrasonic tomographic image will be understood with a single glance. This particular indication may be, for example, (1) a line with a particular color different from the remaining lines, (2) a blinking line, and/or (3) a line with a particular style such as a dotted line or a chain line, or a line with a particular width different from the remaining lines.

As will be apparent from the above-description, according to this embodiment, a three-dimensional skin surface image is displayed next to the tomographic image of the desired cross section on the same screen and also, in the skin surface image, the cross section position of the tomographic image is indicated. Therefore, relationship between the tomographic image and the three-dimensional skin surface image can be concretely and objectively recognized so that analysis of injury changes of tissues such as tendon of soft tissue or muscle connective tissue can be easily executed without the assistance of expert image-examination technique. Thus, by using the apparatus of this embodiment, an internal injury such as contusion or sprain can be easily examined without the assistance of expert technique, and also an object having difficulty for examination even by using radiography can be easily examined. Furthermore, this apparatus is easy for operating resulting observation of bone, tendon and muscle tissues to be very easy. Also, since there is no danger of X-ray and no special qualification is necessary for treating this apparatus, anyone can easily use this apparatus. It is a further advantage that this apparatus can be manufactured very cheaper than the another diagnostic apparatus such as a CT scanning apparatus.

Figure 11:
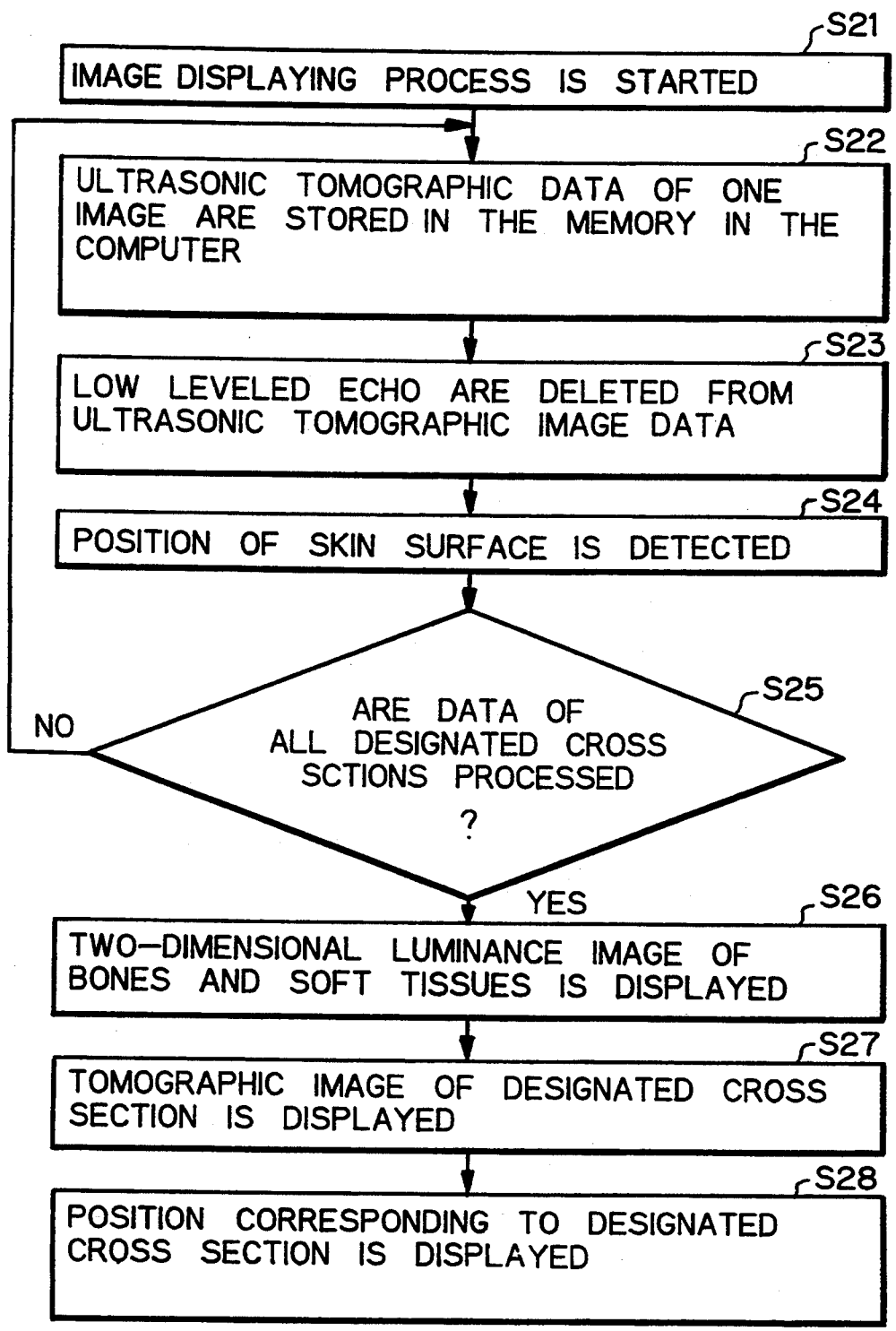
FIG. 11 is a flow chart of a control program for controlling display of images in an another embodiment according to the present invention.

FIG. 11 is a flow chart of a control program for controlling display of images in an another embodiment of a multi-dimensional visualization apparatus for observing tissue according to the present invention.

In this embodiment, a structure of the visualization apparatus and a control process of inputting ultrasonic tomographic image data are substantially the same as those of the aforementioned embodiment indicated in FIGS. 1 to 4. Therefore, in the following description, the similar components are denoted by the same reference numerals, respectively.

When the operator applies a command for displaying tomographic image to the computer 14 by means of the keyboard 14a or the mouse 14b, an image displaying process will be started at step S21. At the next step S22, ultrasonic tomographic data of one image (of one cross section) are read out from the image memory 13a in the control board 13 and stored in a RAM in the computer 14.

Then, at step S23, low leveled echo portions are deleted from the stored tomographic image data so as to eliminate noise component occurred when the ultrasound passed between the probe 11 and the skin surface.

At step S24, coordinates of the layer surface or the skin surface will be detected. This detection is executed by comparing gradation values of the neighboring pixels of the ultrasonic tomographic image data in sequence along the ultrasound advancing direction to know a position where the difference first becomes a value larger than zero. This position will be recognized as a position on the body surface.

After the above-mentioned processes of the steps S21 to S24 are completed, coordinate data of a line 20 indicating the skin surface derived from the ultrasonic tomographic image data will be stored in the RAM. Why the skin surface position can be detected is as follows. Since, between the probe 11 and the layer surface of the body, there exist only the jellied oil or the water balloon filled with water, ultrasound beam directed from the probe 11 will be first reflected at the skin surface due to the difference of there sound impedances. Therefore, by searching a position where the gradation difference concerning the echo level changes a value other than zero, the skin surface position can be detected.

At step S25, the computer 14 judges whether the aforementioned processes at the steps S22 to S24 are completed for the ultrasonic tomographic data of all the designated images (cross sections) or not. If not, the program returns to the step S22 and the same processes are repeatedly executed. If completed for the all images, the program will proceed to step S26.

At the step S26, two-dimensional echo level data with respect to bones and soft tissues in the body are calculated and a two-dimensional luminance image is displayed on the CRT 14c in accordance with the calculated echo level data. Detailed illustration about the operation of this step S26 is shown in FIG. 12.

Figure 12:
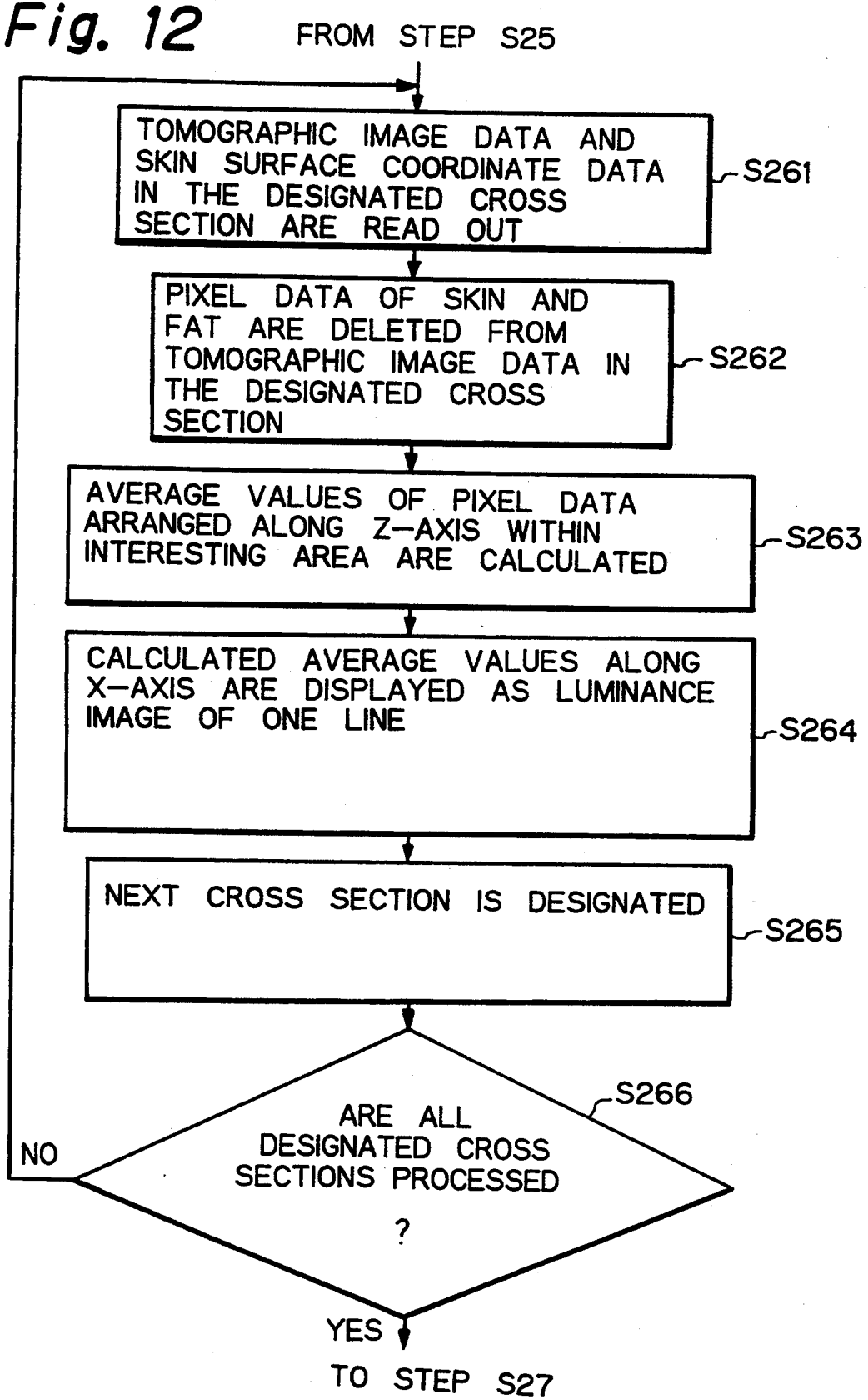
FIG. 12 is a flow chart showing processes of calculating two-dimensional echo level data with respect to bones and soft tissues in the body and of displaying a two-dimensional image in accordance with the calculated echo level data, in the program shown in FIG. 11.

At step S261 of FIG. 12, the tomographic image data and coordinate data of the skin surface, in a certain cross section of the body designated by the pointer, are read out from the RAM of the computer 14. Then, at step S262, the pixel data corresponding to skin and fat beneath the skin in the body are deleted from the stored tomographic image data in a designated cross section. The depth of the skin and the fat beneath the skin will be predetermined as a variable surface compensation value. Therefore, an area of the pixel data to be deleted can be easily determined in accordance with the skin surface coordinate data and the predetermined surface compensation value.

At the next step S263, an average value of the pixel data of the tomographic image, arranged along the advancing direction of ultrasound (Z-axis) within a variable interesting area 42a (shown in FIG. 13) is calculated for each column. This calculation may be carried out by summing the values of all the pixel data on each column within the interesting area and by dividing the summed value by the number of pixels of the corresponding column within the interesting area. Thus, average values of all the columns (of one line) will be calculated at this step. The interesting area in this embodiment can be predetermined by specifying the depth of the end line of this area from the skin surface and will be selected so that an image of bones and soft tissues to be observed are contained within this area.

Figure 13:
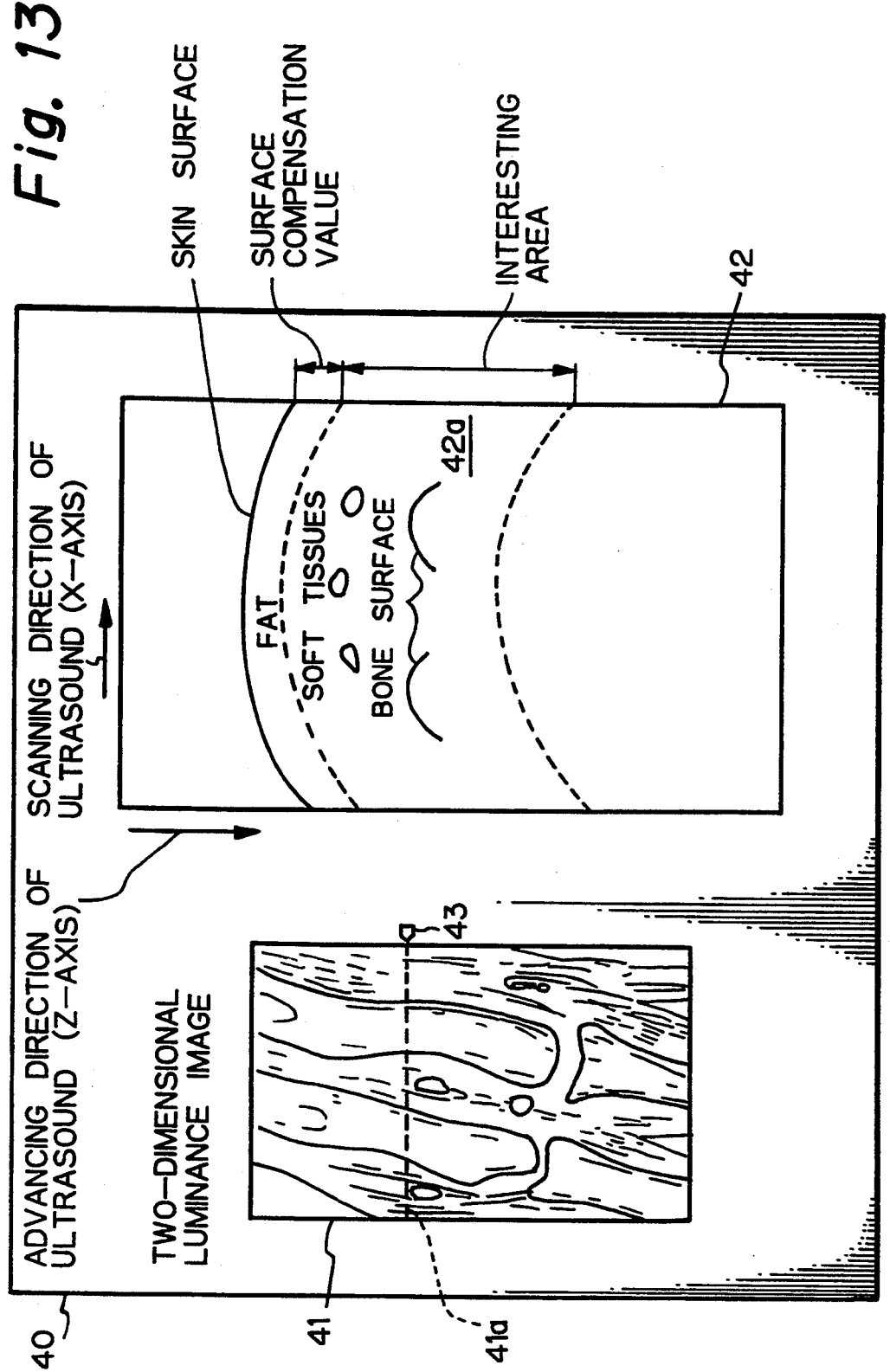
FIG. 13 illustrates an example of an image displayed by the program of FIG. 11.

Then, at step S264, the calculated average values along X-axis corresponding to the designated cross section are displayed on the CRT 14c as a luminance image (in 256 gradations) of one line (for example an image along a dotted line 41a shown in FIG. 13).

At the next step S263, the pointer is incremented so that tomographic image data of the next cross section are designated. Thereafter, at step S264, the computer 14 judges whether the aforementioned processes at the steps S261 to S265 are completed for the coordinate data of all the designated cross sections or not. If not, the program returns to the step S261 and the same processes are repeatedly executed. If completed for the all cross sections, the program will proceed to step S27 of FIG. 11.

Thus, as shown in FIG. 13, a two-dimensional luminance image 41, like a radiograph, indicating the bones and soft tissues in the hand is displayed on the CRT 14c of the computer 14.

At the step S27 of FIG. 11, a tomographic image 42 of the designated cross section, stored in the RAM of the computer 14, is read out and displayed on the same screen 40 as the two-dimensional luminance image 41 of the bones and soft tissues, as shown in FIG. 13. At the next step S28, a mark 43 indicating a position of the designated cross section is displayed on the side of the two-dimensional luminance image 41 so that the relationship between the two-dimensional luminance image 41 and the ultrasonic tomographic image 42 will be understood with a single glance. This display of the mark 43 may be, for example, (1) a mark with a particular color different from the remaining image, (2) a blinking mark, and/or (3) a mark with a particular line such as a dotted line or a chain line, or a blinking line.

A desired cross section may be designated by moving the mark 43 on the screen 40 by means of for example the keyboard 14a or the mouse 14b resulting that a tomographic image corresponding to the designated cross section is displayed on the screen 40.

As will be apparent from the above-description, according to this embodiment, a two-dimensional luminance image of bones and soft tissues can be displayed next to the tomographic image of the desired cross section on the same screen and also the cross section position of the tomographic image is indicated by for example a mark. Therefore, relationship between the tomographic image and the two-dimensional luminance image can be concretely and objectively recognized so that analysis of injury changes of tissues such as bones and soft tissues can be easily executed without the assistance of expert image-examination technique. Thus, by using the apparatus of this embodiment, an internal injury such as contusion or sprain can be easily examined without the assistance of expert technique, and also an object having difficulty for examination even by using radiography can be easily examined. Furthermore, this apparatus is easy for operating resulting observation of bones and soft tissues to be very easy. Also, since there is no danger of X-ray radiation and no special qualification is necessary for treating this apparatus, anyone can easily use this apparatus. It is a further advantage that this apparatus can be manufactured very cheaper than the another diagnostic apparatus such as a CT scanning apparatus.

In the above-mentioned embodiment, the two-dimensional image of the bones and soft tissues is displayed in a luminance image. However, this image may be displayed with different colors for respective gradation values so as to clearly indicate bones injury changes within a body.

Figure 14:
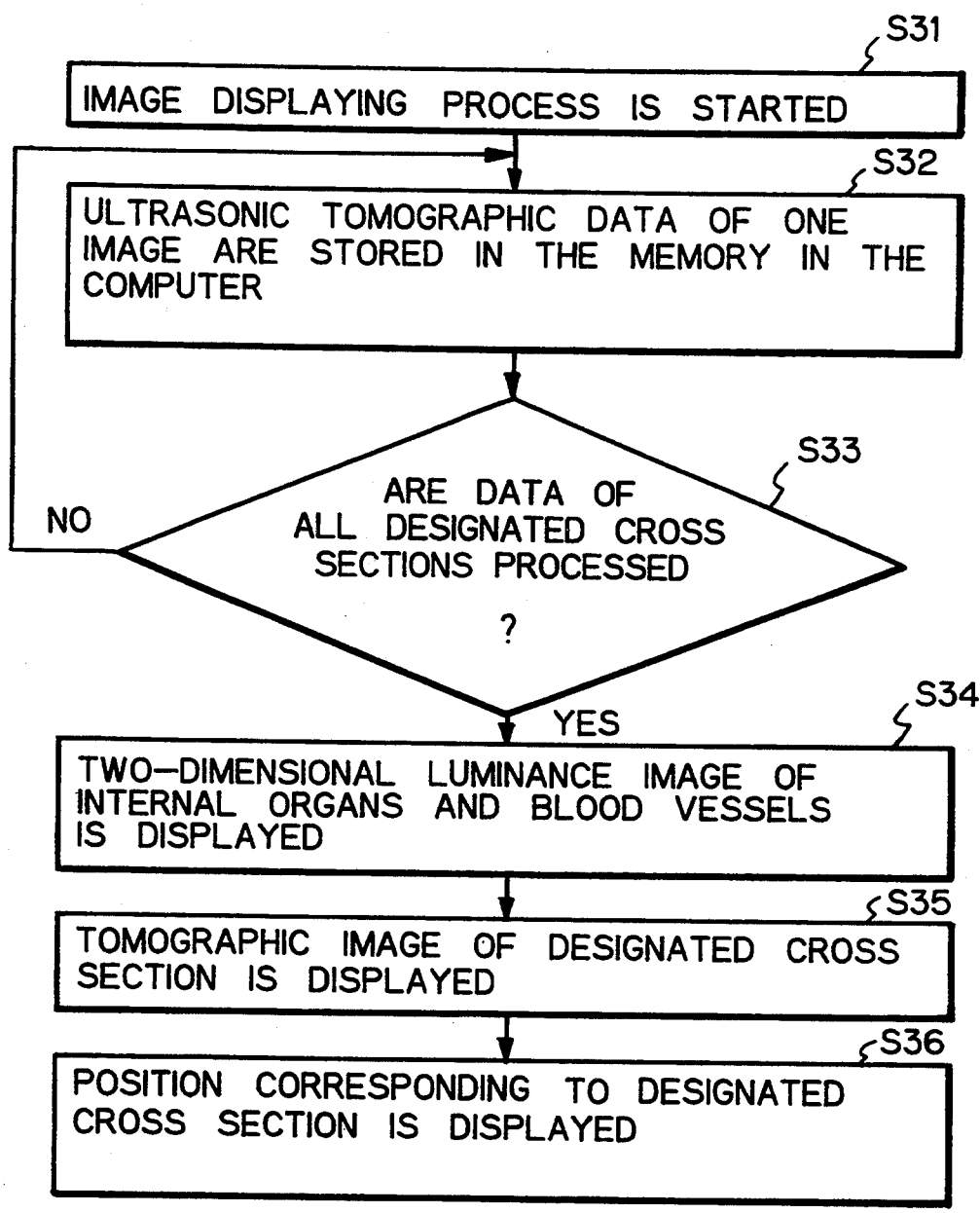
FIG. 14 is a flow chart of a control program for controlling display of images in a further embodiment of a multi-dimensional visualization apparatus for observing tissue according to the present invention.

FIG. 14 is a flow chart of a control program for controlling display of images in a further embodiment of a multi-dimensional visualization apparatus for observing tissue according to the present invention.

In this embodiment, a structure of the visualization apparatus and a control process of inputting ultrasonic tomographic image data are substantially the same as those of the aforementioned embodiment indicated in FIGS. 1 to 4. Therefore, in the following description, the similar components are denoted by the same reference numerals, respectively.

When the operator applies a command for displaying tomographic image to the computer 14 by means of the keyboard 14a or the mouse 14b, an image displaying process will be started at step S31. At the next step S32, ultrasonic tomographic data of one image (of one cross section) are read out from the image memory 13a in the control board 13 and stored in a RAM in the computer 14.

Then, at step S33, the computer 14 judges whether the aforementioned process at the step S32 is completed for the ultrasonic tomographic data of all the designated images (cross sections) or not. If not, the program returns to the step S32 and the same process is repeatedly executed. If completed for the all images, the program will proceed to step S34.

At the step S34, two-dimensional echo level data with respect to blood vessels and organs in the body are calculated and a two-dimensional luminance image is displayed on the CRT 14c in accordance with the calculated echo level data. Detailed illustration about the operation of this step S34 is shown in FIG. 15.

Figure 15:
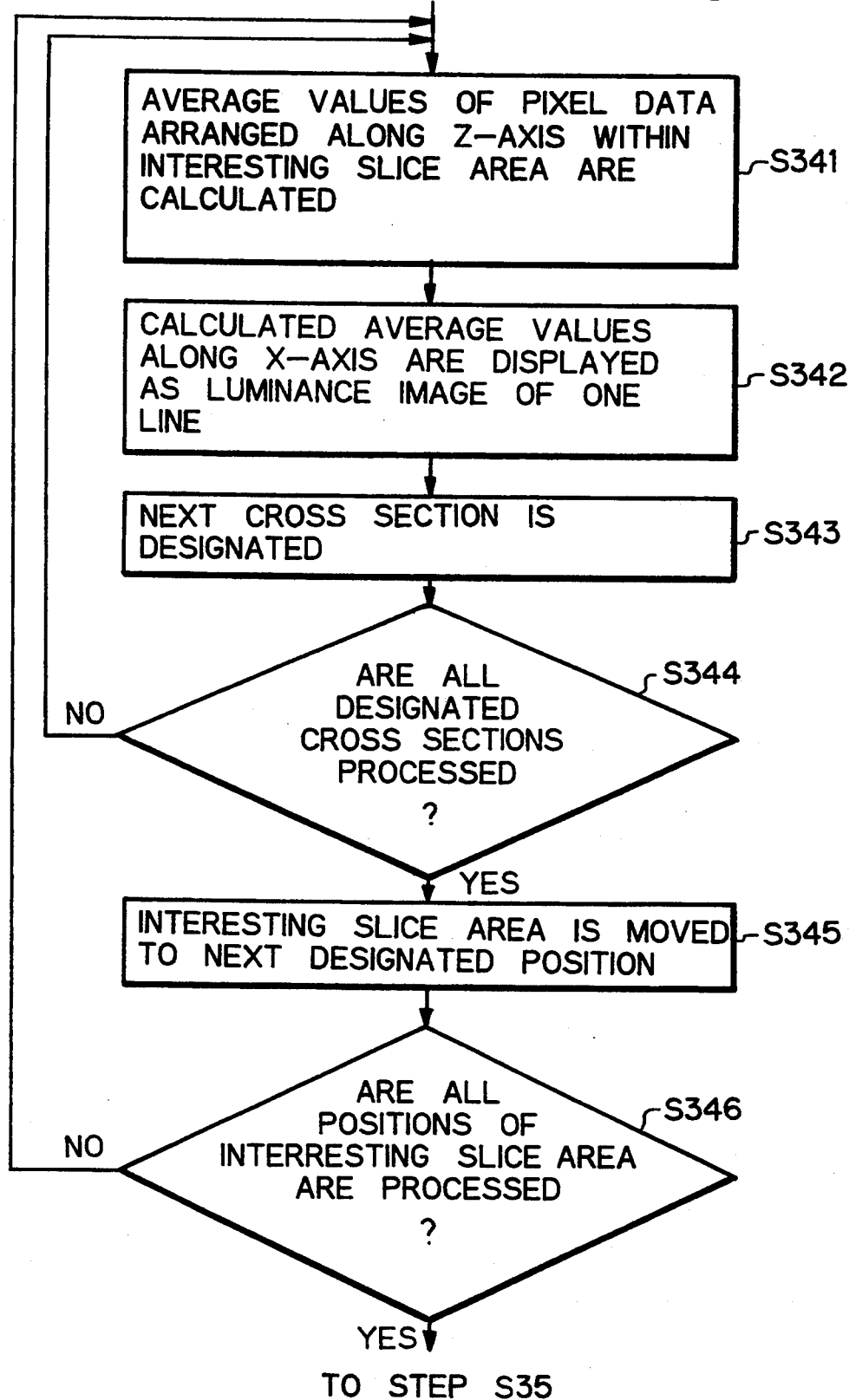
FIG. 15 is a flow chart showing processes of calculating two-dimensional echo level data with respect to blood vessels and organs in the body and of displaying a two-dimensional image in accordance with the calculated echo level data, in the program shown in FIG. 14.

At step S341 of FIG. 15, an average value of the pixel data of the tomographic image in a designated cross section of the body, arranged along the advancing direction of ultrasound (Z-axis) within an interesting slice area 52a (shown in FIG. 16) at a designated position of Z-axis coordinate is calculated for each column. This calculation may be carried out by summing the values of all the pixel data on each column within the interesting slice area 52a and by dividing the summed value by the number of pixels of the corresponding column within the interesting slice area. Thus, average values of all the columns (of one line) will be calculated at this step. The width of the interesting slice area 52a is small but can be variably selected. In this embodiment, the interesting slice area 52a is formed in a strip shape extending in parallel with the X-axis as shown in FIG. 16. However, this area may be shaped as a strip 52b inclined to the X-axis.

Then, at step S342, the calculated average values along X-axis corresponding to the designated cross section are displayed on the CRT 14c as a luminance image (in 256 gradations) of one line (for example an image along a dotted line 51a shown in FIG. 16).

At the next step S343, the pointer is incremented so that tomographic image data of the next cross section are designated. Thereafter, at step S344, the computer 14 judges whether the aforementioned processes at the steps S341 to S343 are completed for all the designated cross sections or not. If not, the program returns to the step S341 and the same processes are repeatedly executed. If completed for the all cross sections, the program will proceed to the next step S345.

At this stage, as shown in FIG. 16, a two-dimensional luminance image 51, like a radiograph, indicating the blood vessels and organs in the body is displayed on the CRT 14c of the computer 14.

At the step S345, the interesting slice area 52a is moved to a next designated position of Z-axis coordinate. This next position may be designated to a slice area adjacent to the current interesting slice area in the Z-axis direction in sequence, or to a slice area at a desired position of Z-axis coordinate. Then, at step S346, the computer 14 Judges whether the aforementioned processes at the steps S341 to S345 are completed for all necessary positions of the interesting slice area or not. If not, the program returns to the step S341 and the same processes are repeatedly executed. If completed for the all positions, the program will proceed to step S35 of FIG. 15. By moving the interesting slice area, the best position for displaying a two-dimensional luminance image which is proper to observe the blood vessels and organs in the body will be found.

At the step S35 of FIG. 14, a tomographic image 52 of the designated cross section, stored in the RAM of the computer 14, is read out and displayed on the same screen 50 as the two-dimensional luminance image 51 of the blood vessels and internal organs, as shown in FIG. 16. At the next step S36, a mark 53 indicating a position of the designated cross section is displayed on the side of the two-dimensional luminance image 51 so that the relationship between the two-dimensional luminance image 51 and the ultrasonic tomographic image 52 will be understood with a single glance. This display of the mark 53 may be, for example, (1) a mark with a particular color different from the remaining image, (2) a blinking mark, and/or (3) a mark with a particular line such as a dotted line or a chain line, or a blinking line.

A desired cross section may be designated by moving the mark 53 on the screen 50 by means of for example the keyboard 14a or the mouse 14b resulting that a tomographic image corresponding to the designated cross section is displayed on the screen 50.

As will be apparent from the above-description, according to this embodiment, a two-dimensional luminance image of blood vessels and internal organs can be displayed next to the tomographic image of the desired cross section on the same screen and also the cross section position of the tomographic image is indicated by for example a mark. Therefore, relationship between the tomographic image and the two-dimensional luminance image can be concretely and objectively recognized so that analysis of injury changes of tissues such as blood vessels and internal organs can be easily executed without the assistance of expert image-examination technique. Thus, by using the apparatus of this embodiment, an internal injury can be easily examined without the assistance of expert technique, and also an object having difficulty for examination even by using radiography can be easily examined. Furthermore, this apparatus is easy for operating resulting observation of blood vessels and internal organs to be very easy. Also, since there is no danger of X-ray radiation and no special qualification is necessary for treating this apparatus, anyone can easily use this apparatus. It is a further advantage that this apparatus can be manufactured very cheaper than the another diagnostic apparatus such as a CT scanning apparatus.

In the above-mentioned embodiment, the two-dimensional image of the blood vessels and internal organs is displayed in a luminance image. However, this image may be displayed with different colors for respective gradation values so as to clearly indicate injury changes within a body.

In addition to the above-mentioned basic functions, the apparatus of the present invention may have functions of (1) displaying a tomographic image with different colors for respective gradation values so as to clearly indicate injury changes within a body, (2) displaying a tomographic image with different colors for respective tissues and also with different luminance for respective gradation values so as to clearly indicate injury changes within a body, and/or (3) displaying a composite tomographic image synthesized by a plurality of tomographic images obtained by discriminating various kinds of objects to be examined with a plurality of ultrasound frequencies.

Most of bones, tendons and muscle tissues near the body surface have a less difference between individual bodies and there will be similar relationships between the individual bodies, respectively. Therefore, it may be very useful for analyzing a measured ultrasonic tomographic image to display a standard tomographic image of the corresponding tissue structure on the same screen and to compare them with each other.

By displaying thermal distribution on the body surface measured by the thermal video observation device 15 on the same screen as the ultrasonic tomographic image, both injury changes of such as tendon or muscle connective tissue (from the tomographic image) and its inflammation state (from the thermal distribution of the body surface) can be simultaneously observed.

By displaying an image indicating for example tension changes of muscle tissues obtained from the moire pattern observation device 16 on the same screen as the ultrasonic tomographic image, both injury tension of the tissue (from the tomographic image) and the tension changes of the skin (from the moire pattern of the body surface) can be simultaneously observed resulting that injury changes of the soft tissues which have been invisible can be easily observed from inside and outside of the body.

Many widely different embodiments of the present invention may be constructed without departing from the spirit and scope of the present invention. It should be understood that the present invention is not limited to the specific embodiments described in the specification, except as defined in the appended claims.

What is claimed is:

1. A multi-dimensional visualization apparatus for observing tissue, comprising:

means for producing ultrasonic tomographic image data with respect to respective parallel cross sections of tissue to be observed;

memory means for temporarily storing the tomographic image data of the respective cross sections, the tomographic image data being received from said producing means;

means for detecting layer surface positions in the respective cross sections of the tissue based upon the tomographic image data stored in the memory means and for producing layer surface coordinate data indicative of the detected layer surface positions;

coordinate transformation means for converting the layer surface coordinate data of the respective cross sections from said detecting means into three-dimensional coordinate data; and means for displaying, on the same screen, both a three-dimensional image of the layer surface positions in the respective cross sections of the tissue based upon the converted three-dimensional coordinate data and the tomographic image of a desired cross section based upon the tomographic image data stored in the memory means.

2. An apparatus as claimed in claim 1, wherein said coordinate transformation means includes means for converting the layer surface coordinate data of the respective cross sections into three-dimensional coordinate data of lines for the respective cross sections, wherein said displaying means includes means for displaying, on the same screen, both a three-dimensional image of the layer surface positions in the respective cross sections by the respective lines and the tomographic image of the desired cross section.

3. An apparatus as claimed in claim 2, wherein said displaying means includes means for indicating a particular line of the desired cross section so that said line can be identified from the remaining displayed lines.

4. An apparatus as claimed in claim 3, wherein said indicating means includes means for indicating a particular line of the desired cross section with a color different from that of the remaining displayed lines.

5. An apparatus as claimed in claim 3, wherein said indicating means includes means for indicating a particular line of the desired cross section with a blinking line.

6. An apparatus as claimed in claim 3, wherein said indicating means includes means for indicating a particular line of the desired cross section with a width different from that of the remaining displayed lines.

7. An apparatus as claimed in claim 3, wherein said indicating means includes means for indicating a particular line of the desired cross section with a style different from that of the remaining displayed lines.

8. An apparatus as claimed in claim 1, wherein said detecting means includes means for eliminating a low-level echo component from contents of the tomographic image data stored in the memory means.

9. An apparatus as claimed in claim 8, wherein said tomographic image is of a plurality of pixel data, wherein said eliminating means includes means for forcibly changing contents of the pixel data, having values equal to or less than a predetermined value, to zero.

10. An apparatus as claimed in claim 9, wherein said detecting means includes means for comparing values of the neighboring pixel data of the tomographic image data in sequence along an ultrasound advancing direction to detect a position where a difference between the compared values changes to a value larger than zero.

11. An apparatus as claimed in claim 1, wherein said apparatus further comprises means for measuring thermal distribution on a body surface and means for displaying the measured thermal distribution on the same screen as the tomographic image.

12. An apparatus as claimed in claim 1, wherein said apparatus further comprises means for producing a moire pattern on a body surface and means for simultaneously displaying an image indicating outside changes of the body surface obtained from the moire pattern producing means and the tomographic image on the same screen.

13. A multi-dimensional visualization apparatus for observing tissue, comprising:
    means for producing ultrasonic tomographic image data with respect to respective parallel cross sections of tissue to be observed, said ultrasonic tomographic image data of the each cross section being comprised of a plurality of pixel data to be arranged in an ultrasound advancing direction and an ultrasound scanning direction;
    memory means for temporarily storing the tomographic image pixel data in the respective cross sections, the tomographic image pixel data being received from said producing means;
    means for calculating average values of the stored tomographic image pixel data along the ultrasound advancing direction within a designed interesting area, said calculation of the average values being executed in each one of the cross sections of the tissue to produce two-dimensional image data; and
    means for displaying, on the same screen, both a two-dimensional image of the tissue based upon the produced two-dimensional image data and the tomographic image of a desired cross section based upon the tomographic image data stored in the memory means.

14. An apparatus as claimed in claim 13, wherein said displaying means includes means for displaying, on the same screen, the tomographic image of the desired cross section and the two-dimensional image with a mark for indicating a position of the displayed cross section.

15. An apparatus as claimed in claim 13, wherein said displaying means displays said two-dimensional image in various luminance intensities depending upon the produced two-dimensional image data.

16. An apparatus as claimed in claim 13, wherein said display means displays said two-dimensional image in different colors depending upon the produced two-dimensional image data.

17. An apparatus as claimed in claim 13, wherein said apparatus further comprises means for detecting layer surface positions in the respective cross sections of the tissue based upon the tomographic image pixel data stored in the memory means, to produce layer surface coordinate data indicative of the detected layer surface positions, and means for deleting the tomographic image pixel data stored in the memory means, in the respective cross sections of the tissue based upon the layer surface coordinate data and a designated surface compensation value.

18. An apparatus as claimed in claim 17, wherein said designated interesting area is specified by at least the layer surface coordinate data and a desired variable depth.

19. An apparatus as claimed in claim 17, wherein said detecting means includes means for eliminating a low-level echo Component from contents of the tomographic image data stored in the memory means.

20. An apparatus as claimed in claim 19, wherein said eliminating means includes means for forcibly changing contents of the pixel data having values equal to or less than a predetermined value, to zero.

21. An apparatus as claimed in claim 20, wherein said detecting means includes means for comparing values of the neighboring pixel data of the tomographic image data in sequence along an ultrasound advancing direction to detect a position where a difference between the compared values changes to a value larger than zero.

22. An apparatus as claimed in claim 13, wherein said designated interesting area is a designated interesting slice area with a strip shape.

23. An apparatus as claimed in claim 22, further comprising means for moving said interesting slice area in the ultrasound advancing direction to a next designated area.

24. An apparatus as claimed in claim 22, wherein said interesting slice area extends in parallel with the ultrasound scanning direction or is inclined to the ultrasound scanning direction.

25. An apparatus as claimed in claim 13, wherein said apparatus further comprises means for measuring thermal distribution on a body surface and means for displaying the measured thermal distribution on the same screen as the tomographic image.

26. An apparatus as claimed in claim 13, wherein said apparatus further comprises means for producing a moire pattern on a body surface and means for simultaneously displaying an image indicating outside changes of the body surface obtained from the moire pattern producing means and the tomographic image on the same screen.

* * * * *